United States Patent [19]

Park

[11] Patent Number: 4,646,557
[45] Date of Patent: Mar. 3, 1987

[54] DYNAMIC FORCE MEASUREMENT SYSTEM

[75] Inventor: Kyong Park, Chatsworth, Calif.

[73] Assignee: Kavilco Corporation, Chatsworth, Calif.

[21] Appl. No.: 834,885

[22] Filed: Feb. 28, 1986

[51] Int. Cl.$^4$ ............................................. G01N 19/02
[52] U.S. Cl. ........................................................ 73/9
[58] Field of Search ............................ 73/9; 369/53, 58

[56] References Cited

U.S. PATENT DOCUMENTS

| | | | |
|---|---|---|---|
| 1,772,415 | 8/1930 | Carpenter | 73/9 |
| 3,376,730 | 4/1968 | Clement et al. | 73/9 |
| 3,721,115 | 3/1973 | Kearns | 73/9 |
| 3,813,917 | 6/1974 | Cole | 73/9 |
| 4,416,144 | 11/1983 | Chen et al. | 73/432 V X |

FOREIGN PATENT DOCUMENTS

| | | | |
|---|---|---|---|
| 1066037 | 9/1959 | Fed. Rep. of Germany | 73/9 |
| 2967 | 1/1980 | Japan | 73/9 |
| 299761 | 5/1971 | U.S.S.R. | 73/9 |
| 563606 | 6/1977 | U.S.S.R. | 73/9 |
| 731291 | 4/1980 | U.S.S.R. | 73/9 |
| 1045088 | 9/1983 | U.S.S.R. | 73/9 |

OTHER PUBLICATIONS

"Apparatus for Studying the Behavior of Sliding Electrical Contacts at very High Speeds"; *The Review of Scientific Instruments*, vol. 42, No. 8, pp. 1250-1252; Aug. 1971; P. E. McElligot.

*Primary Examiner*—Stewart J. Levy
*Assistant Examiner*—Tom Noland
*Attorney, Agent, or Firm*—Poms, Smith, Lande & Rose

[57] ABSTRACT

The coefficient of the dynamic friction of the surface of a memory disk or disks may be measured by tilting the entire memory unit, with the magnetic head being mounted for limited movement in the direction of relative movement of the head and the surface. The movement of the memory disk initially carries the head to its extreme position in the direction of movement of the disk. At a certain angle, as the memory unit is tilted from the horizontal toward the vertical, the weight of the head will overcome the dynamic force of the disk-head drag and the head movement to its lower position will be sensed; and the operative component of the weight of the head and its mount at the critical angle will be substantially equal to the dynamic drag or frictional force between the head and the associated disk or disks.

9 Claims, 5 Drawing Figures

DYNAMIC FORCE MEASUREMENT SYSTEM

FIELD OF THE INVENTION

This invention relates to systems for measuring the dynamic coefficient of friction.

BACKGROUND OF THE INVENTION

For the design of disk type magnetic storage systems it is useful to determine the force applied to a magnetic head and its mounting at various relative speeds, including high speed rotation of the disk, when the head is normally spaced slightly from the disk and "flies" over the disk surface.

Various techniques have been proposed heretofore for measuring static and dynamic friction. Typical publications showing such systems include C. E. Carpenter U.S. Pat. No. 1,772,415; F.D. Long, U.S. Pat. No. 3,020,744; and Japanese Patent Application 53-61515, published Dec. 1, 1979. These patents disclose variable angle planes to determine static friction, and the Japanese disclosure indicates the use of an accelerometer to provide a more complete picture of the movement of an object on a slanted plane. However, none of these systems discloses a method or apparatus for determining the drag or frictional force between two objects which are moving relative to one another under constant or stable dynamic conditions.

Accordingly, a principal object of the present invention is to provide a simple and inexpensive technique for determining the force or drag between a magnetic head and a rotating magnetic disk, or other similar relatively movable objects.

SUMMARY OF THE INVENTION

In accordance with an important aspect of the present invention the force or drag between a magnetic head or slider and an associated magnetic memory disk may be determined by mounting the head for normal operation relative to the rotating magnetic disk, but with limited movement in the direction of the relative movement of the head and disk. Sensing arrangements, such as microswitches or LED-Phototransistor pairs, are mounted to sense when the head shifts between its two extreme positions. The entire disk memory unit is then mounted for tilting from the horizontal with the axis of tilting being substantially perpendicular to a line defining the direction of relative movement of the disk at the magnetic head. When the unit is horizontal, the head is dragged by the rotating disk or disk assembly to one extreme position of its limited permitted range of movement, and this position is sensed by the blocking of one phototransistor or the energization of one microswitch. Then, as the entire disk unit is tilted further from the horizontal, the operative component of the weight of the magnetic head will exceed the drag of the rotating disk, and the head will shift slightly to its lower alternative position. This shift will be indicated by the sensing devices. From the angle at which the position of the head shifts, the force applied between the rotating disk and the head may be calculated.

The same principle can also be applied more generally to determine drag force or sliding friction using a rotating disk and an object mounted for limited or constrained movement on the surface of the disk, and sensing the shift of position fo the object, and the corresponding tilt angle, in order to determine the dynamic force.

Other objects, features, and advantages of the invention will become apparent from a consideration of the following detailed description and from the accompanying drawings.

DETAILED DESCRIPTION

Figure 1:
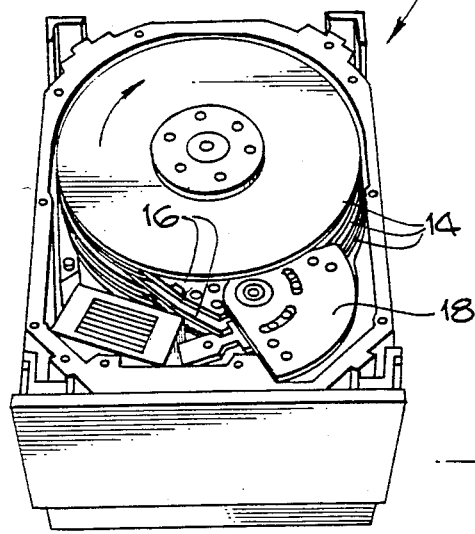
FIG. 1 is a perspective view of a digital memory unit generally of conventional construction, but with its cover removed, the unit being modified slightly as will be described in some detail hereinbelow.

Referring more particularly to the drawings, FIG. 1 shows a commercially available hard disk digital magnetic memory, which has been modified slightly to implement the purposes of the present invention. In FIG. 1, the memory unit 12 includes a series of hard disks 14 which are rotated together at relatively high speeds. Secured to the mounting arms 16 between the disks are a number of magnetic heads which are employed for reading and writing digital information onto the hard disks 14 in terms of very small zones of magnetization. Part of the actuator 18 for moving the arms 16 is apparent in the showing of FIG. 1, which incidentally has the top cover removed from the unit.

Figure 2:
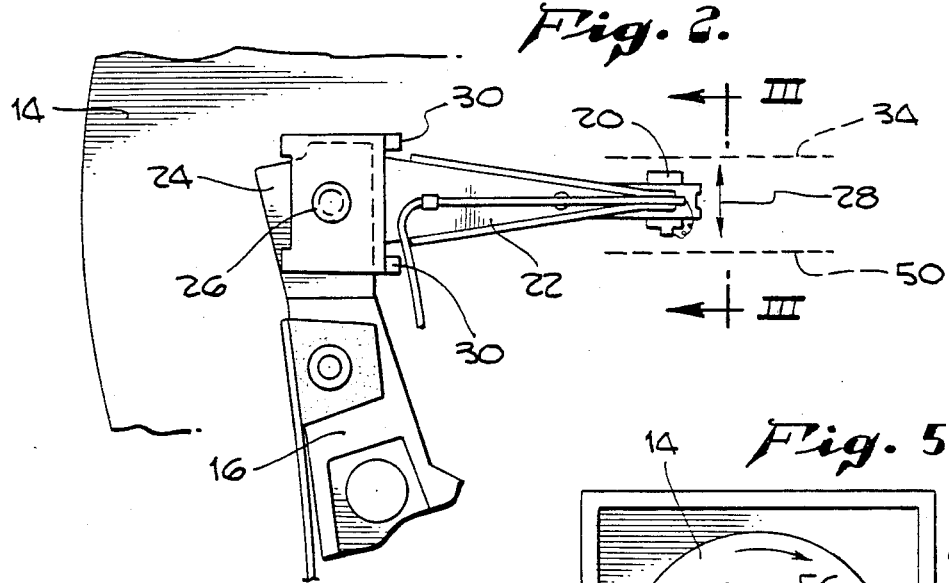
FIG. 2 shows a movable magnetic head and mounting arm arrangements therefor, and illustrating principles of the present invention.
Figure 3:
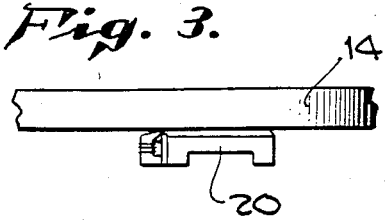
FIG. 3 is a view taken along lines III—III of FIG. 2.

FIG. 2 is a somewhat more detailed showing of one of the arms 16, with the magnetic head 20 mounted at the outer end thereof. Normally, the laterally extending portion 22 to which the head 20 is affixed, is rigidly secured to the outer end 24 of arm 16. However, in the present case, the arm 22 is pivotally mounted to the end 24 of arm 16 by a single fastener 26 permitting limited rotational movement of arm 22 about fastener 26, as indicated by the arrow 28. Incidentally, the members or tabs 30 which are secured to the laterally extending arm 22, extend downwardly and engage the outer end 24 of arm 16 to preclude any significant movement of the head 20, beyond about, for example, ¼ of an inch.

Now, with the disks 14 rotating at high speed in the counterclockwise direction, the head 20 will shift to its uppermost position as indicated by the dashed line 34 in FIG. 2, as a result of the drag or force exerted by the high speed rotation of the disks 14. Initially, of course, as the head 20 is touching one of the disks 14, there will be direct frictional force involved; however, as the speed of the disks increase, the heads are normally spaced apart slightly from the disks as a result of air pressure, and the heads assume a "flying height" which spaces them several thousandths of an inch above the surface of the disks. Measurements of dynamic friction may be made at various speeds of rotation of the disks, with the heads or sliders in engagement with the disks, and at higher normal operational speeds.

Figure 4:
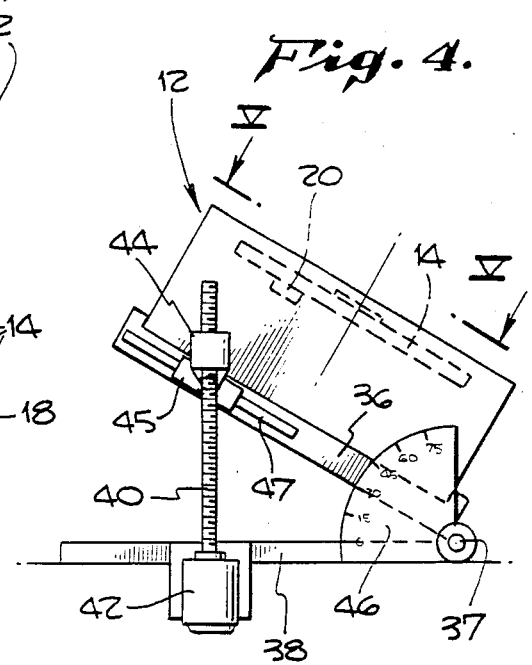
FIG. 4 is a side view showing tilting arrangements for changing the angular orientation of the digital memory unit of FIG. 1.

As shown in FIG. 4, the memory unit 12 may be mounted on a tilting shelf or rack 36 which may be adjustably tilted around the hinge or pivot point 37, relative to a horizontal base member 38. A threaded bolt 40 is secured to the drive shaft of motor 42 which in turn is secured to the base plate 38. A nut 44 is pivotally secured to slider 45 which rides in a track 47 in the edge of the tilting plate or shelf 36, so that as the threaded shaft 40 rotates in engagement with the threads of the nut 44, the shelf 36 tilts to the desired angle, all under the control of motor 42. The angle of tilt of the shelf 36 and the unit 12 may be determined from the protractor or scale 46 which indicates the angle of inclination of the shelf 36 relative to the base plate 38. The unit 12 is mounted on the shelf 36 so that the direction of relative movement of the head 20 and the disk 14 as indicated by the arrow 48, is pointing upwardly parallel with the near edge of the shelf or bracket 36 of FIG. 4. Accordingly, as the unit 12 is raised, as shown in FIG. 4, the weight of the head 20 and the arm 22 will tend to suppy a force to shift the head 20 toward the lower dashed line 50 as shown in FIG. 2 in opposition to the drag or the rotational force or impetus provided by the rotating disk 14 which tends to move the head 20 toward the dashed line 34, as shown in FIG. 2.

Figure 5:
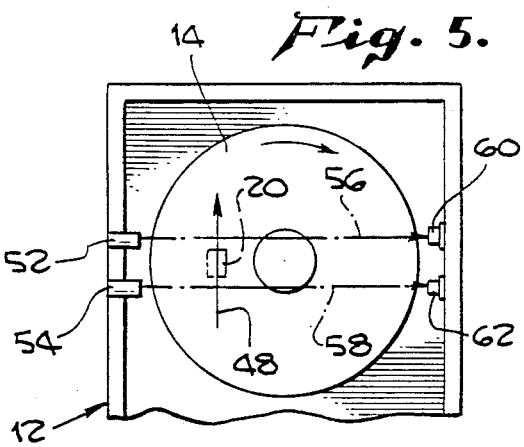
FIG. 5 is a schematic top view illustrating the photosensitive detection arrangements for sensing shifts in the position of the magnetic head.

At a certain angle of the shelf or bracket 36 relative to the base plate 38, of FIG. 4, the head 20 will shift from one extreme position as indicated by the dashed line 34 to the other extreme position as indicated by the dashed line 50, in FIG. 2. Sensing arrangments such as the light-emitting diodes 52 and 54, which are mounted in elongated light-directing tubes, provide beams of illumination 56 and 58, respectively, which impinge on phototransistors 60 and 62, respectively, when the light beams are not interrupted by the movement of the head 20 to block one of the two beams. If desired, a single light-emitting diode and phototransistor could be employed; however, the interruption of one of the two beams together with the energization of the other phototransistor provides a more positive indication that the shifting in position of the head 20 has indeed occurred. Instead of using the light-emitting diodes and the phototransistors, as shown in diagramatically FIG. 5, very small microswitches may be employed, and mounted on the arm 16, and a determination made as to the pivotting of the arm 22 relative to the arm 16 obtained by the actuation of these microswitches.

Concerning the calculation of the drag force or frictional force between the head or slider 20 or other object and the disk, the effective mass of the head 20 and the pivotted arm 22 are initially calculated. This may be accomplished by mounting the arm 16 substantially vertically and employing a scale, balance, or other force measuring device, to measure the effective weight of the arm 22 and the head 20. Then, with the unit 12 mounted on the bracket 36 so that, in operation, the main portion of the arm 16 is substantially parallel with the edge of the tilting shelf or bracket 36, the angle is determined from the scale 46, at which the head shifts position from its uppermost location to its lower position. The effective weight of the head 20 and arm 22 is then multiplied by the sine of the angle between the shelf 36 and the base plate 38, and the resultant figure is substantially equal to the drag or frictional force between the head 20 and the rotating disks 14, which has now been overcome.

In conclusion, it is to be understood that the foregoing description and the accompanying drawings relate to one illustrative embodiment of the invention. In this regard, instead of employing a pivoted head, when sliding friction is to be determined under dynamic conditions, an enclosing bracket or cage may be provided which will hold an object in a desired location on a rotating disk, but permit limited movement of the object. Initially this movement would be in one direction as a result of drag or friction between the rotating disk and the object; and subsequently the object would shift location in the opposite direction, as a result of the weight of the object, as the entire assembly is tilted. In addition, as mentioned above, instead of using light beams to determine the movement of the object, microswitches, or other sensing devices may be employed. It is also noted that in some cases two heads are mounted on a single arm, with one head associated with an adjacent disk on one side of the pair of heads, and the other head associated with a disk on the other side of the two heads. Accordingly, the present invention is not limited to the arrangements precisely as shown and described hereinabove.

What is claimed is:

1. A system for measuring the frictional force or drag between a magnetic head and a rotating magnetic memory disk, comprising:

a digital magnetic memory unit including at least one magnetic memory disk and means for rotating said disk at a predetermined speed;

means for mounting a magnetic head or slider close to one side of said disk, with said head being permitted limited movement in the direction of relative movement of said head and disk, said head being normally shifted to its extreme position in the direction of rotation of said disk when the memory unit and disk are substantially horizontal;

means for adjustably tilting said memory unit along an axis substantially perpendicular to said direction of relative movement so that a component of the weight of said head opposed the frictional force or drag of the rotating disk;

means for indicating the angle of tilt of said magnetic unit;

means for sensing the position of said head to determine when the effective weight of said head and said mounting means directly associated therewith is greater than the frictional force or drag of the rotating disk so that the head shifts to its lower extreme position;

whereby the frictional force or drag of said disk on said head may be calculated from the angle of tilt of said unit when the head shifts position.

2. A system as defined in claim 1 wherein said position sensing means includes a pair of light beam producing and sensing means.

3. A system as defined in claim 1 including a base plate and a tilting shelf secured to said base plate for changing the orientation of said memory unit relative to the horizontal.

4. A system as defined in claim 3 further including threaded bolt means for adjustably shifting said shelf relative to said base plate.

5. A system as defined in claim 3 including protractor means for determining the angle of said shelf relative to said base plate.

6. A system for measuring the frictional force or drag between a magnetic head and a rotating magnetic memory disk, comprising:

a digital magnetic memory unit including at least one magnetic memory disk and means for rotating said disk at a predetermined speed;

means for mounting a magnetic head or slider close to one side of said disk, with said head being permitted limited movement in the direction of relative movement of said head and disk, said head being normally shifted to its extreme position in the direction of rotation of said disk when said disk is substantially horizontal;

means for adjustably tilting said memory unit along an axis having a component perpendicular to said direction of relative movement so that a component of the weight of said head opposes the frictional force or drag of the rotating disk as the unit is tilted;

means for indicating the angle of tilt of said magnetic unit;

means for sensing the position of said head to determine when the effective weight of said head and said mounting means directly associated therewith is greater than the frictional force or drag of the rotating disk so that the head shifts to its lower extreme position;

whereby the frictional force or drag of said disk on said head may be calculated from the angle of tilt of said unit when the head shifts position.

7. A system as defined in claim 6 wherein said position sensing means includes a pair of light beam producing and sensing means.

8. A system as defined in claim 6 including a base plate and a tilting shelf secured to said base plate for changing the orientation of said memory unit relative to the horizontal.

9. A system as defined in claim 8 further including threaded bolt means for adjustably shifting said shelf relative to said base plate; and protractor means for determining the angle of said shelf relative to said base plate.

* * * * *